United States Patent [19]

Ohsumi et al.

[11] Patent Number: 5,441,717
[45] Date of Patent: Aug. 15, 1995

[54] PROCESS FOR PRODUCING ANTIMICROBIAL COMPOUNDS

[75] Inventors: Shuichi Ohsumi, Osaka; Koji Sugiura, Nagoya; Hideki Kato, Kuwana, all of Japan

[73] Assignee: Toagosei Chemical Industry Co., Inc., Ltd., Tokyo, Japan

[21] Appl. No.: 63,704

[22] Filed: May 20, 1993

[30] Foreign Application Priority Data

May 21, 1992 [JP] Japan .................................. 4-154356
May 22, 1992 [JP] Japan .................................. 4-155696

[51] Int. Cl.$^6$ .............................................. C01B 25/45
[52] U.S. Cl. ...................................... 423/306; 424/604
[58] Field of Search ...................... 423/306; 424/604

[56] References Cited

U.S. PATENT DOCUMENTS

| | | |
|---|---|---|
| 1,170,056 | 2/1916 | Engelmann . |
| 2,157,861 | 8/1939 | Nikitin et al. ................. 423/306 |
| 3,416,884 | 12/1968 | Stynes et al. .................... 423/181 |
| 4,025,608 | 5/1977 | Tawil et al. . |
| 4,059,679 | 11/1977 | Clearfield . |
| 4,567,157 | 1/1986 | Lam et al. ..................... 423/306 |
| 4,906,464 | 3/1990 | Yamamoto et al. . |
| 4,938,955 | 7/1990 | Niira et al. . |
| 4,938,958 | 7/1990 | Niira et al. . |
| 5,296,238 | 3/1994 | Sugiura et al. ................. 423/306 |

FOREIGN PATENT DOCUMENTS

| | | |
|---|---|---|
| 2015965 | 4/1970 | France . |
| 4106165 | 2/1991 | Germany . |
| 58-77805 | 5/1983 | Japan . |
| 62-83309 | 4/1987 | Japan . |
| 63-265809 | 2/1988 | Japan . |
| 383905 | 4/1991 | Japan . |
| 3083905 | 4/1991 | Japan . |
| 3083906 | 4/1991 | Japan . |
| 275627 | 12/1991 | Japan . |
| 4142340 | 5/1992 | Japan . |
| 2224727 | 5/1990 | United Kingdom . |
| 2238044 | 5/1991 | United Kingdom . |
| 662491 | 5/1979 | U.S.S.R. . |

OTHER PUBLICATIONS

Hagman et al; "The Crystal Structure . . . ", Acta Chemica Scandinavica 22 (1968) No. 6, pp. 1822-1832.
Clearfield et al; "Synthesis of Sodium Dizirconium . . . ", Mat. Res. Bull. (1980), vol. 15, #11, pp. 16033-1610.
Itoh et al; "Synthesis and Properties of Crystalline . . . "; Advances in Ceramics, vol. 24, 1988, pp. 1007-1014.
Alamo et al; "Ultralow-Expansion Ceramics . . . "; Communications Of The American Ceramic . . . , 1984, pp. C78-C80.
S. Komarneni; "Hydrothermal Preparation of the Low-expansion NZP . . . ; Int. . . . High Technology Ceramics 4"; 1988; pp. 31-39.
K. Kazuo; "Sustained Release Microbicide" . . . Chemical Abstracts, vol. 113, 1990, p. 256.
Kirk-Othmer, *Encyclopedia of Chemical Technology*, vol. 17, Third Edition (1982), John Wiley & Sons, p. 428.

Primary Examiner—Wayne Langel
Attorney, Agent, or Firm—Browdy and Neimark

[57] ABSTRACT

A process for producing an antimicrobial compound represented by the following formula [1]:

$$M^1{}_aH_bA^1{}_cM^2{}_2(PO_4)_3 \cdot nH_2O \qquad [1]$$

wherein $M^1$ is at least one metal ion selected from silver, copper, zinc, tin, mercury, lead, iron, cobalt, nickel, manganese, arsenic, antimony, bismuth, barium, cadmium and chromium, $A^1$ is at least one ion selected from alkali metal ion and alkaline earth metal ion, $M^2$ is a tetravalent metal, n is a number which satisfies $0 \leq n \leq 6$, a and b are positive numbers and c is 0 or a positive number, and a, b and c satisfy $ka+b+mc=1$ where k is a valence of $M^1$ and m is a valence of $A^1$, by supporting at least one metal ion selected from silver, copper, zinc, tin, mercury, lead, iron, cobalt, nickel, manganese, arsenic, antimony, bismuth, barium, cadmium and chromium on a phosphate represented by the following formula [2]:

$$A^2{}_dM^2{}_2(PO_4)_3 \cdot nH_2O \qquad [2]$$

wherein $A^2$ is at least one ion selected from alkali metal ion, alkaline earth metal ion and ammonium ion, $M^2$ and n are as defined above and d is $1/m'$ where m' is a valence of $A^2$, characterized in that said phosphate is synthesized by a wet process and furthermore characterized in that a step of supporting hydrogen ion and a step of firing at 500° to 1300° C. are employed.

10 Claims, No Drawings

PROCESS FOR PRODUCING ANTIMICROBIAL COMPOUNDS

FIELD OF THE INVENTION

The present invention relates to a process for producing an antimicrobial compound consisting of a specific phosphate containing a metal ion having antibacterial, antifungal or antialgal activity such as silver, copper, zinc, tin, mercury, lead, iron, cobalt, nickel, manganese, arsenic, antimony, bismuth, cadmium or chromium ion. The antimicrobial compound obtained by the process of the present invention can be used in antimicrobial compositions which comprise the antimicrobial compound mixed with various binders, for coating compositions, adhesives or fillers, or as antimicrobial shaped products which comprise the antimicrobial compound supported on carriers such as fibers, films, papers, or plastics.

BACKGROUND OF THE INVENTION

Ions such as silver, copper, zinc, tin, mercury, lead, iron, cobalt, nickel, manganese, arsenic, antimony, bismuth, barium, cadmium and chromium ions have been known for a long time as metal ions which exhibit antifungal, antibacterial and antialgal activities (hereinafter referred to as "antimicrobial metal ions"), and particularly silver ion has been widely used in the form of an aqueous silver nitrate solution as bactericides or disinfectants. However, the above-mentioned metal ions having antifungal, antibacterial and antialgal activities are, in many cases, toxic for human bodies and have various restrictions in methods of use, storage and disposal, and their uses are limited.

Recently, it has become clear that application of a slight amount of an antimicrobial metal to subjects is enough to exhibit antifungal, antibacterial and antialgal activities, and organic microbicides or antimicrobial compounds comprising antimicrobial metals supported on ion exchange resins or chelate resins, and inorganic microbicides or antimicrobial compounds comprising antimicrobial metals supported on clay minerals, inorganic ion exchangers or porous materials have been proposed as microbicides having antifungal, antibacterial and antialgal activities.

Among the above microbicides, the inorganic microbicides are generally higher in safety, have longer period of time showing antimicrobial effect and are superior in heat resistance as compared with the organic microbicides.

As one of the inorganic microbicides, there are microbicides prepared by replacing an alkali metal ion such as sodium ion in clay minerals such as montmorillonite and zeolite with silver ion, but the skeleton structure of the clay minerals per se is inferior in acid resistance, and therefore the silver ion readily flows away into an acidic solution and the microbicides have no durable antimicrobial effect. Furthermore, silver ion is unstable against exposure to heat and light and is immediately reduced to metallic silver to cause coloration. Thus, these microbicides lack long-term stability.

In order to enhance the stability of silver ion, an attempt has been made to support both silver ion and ammonium ion on zeolite by ion exchanging, but the problem of coloration has not yet been solved to practically acceptable level and fundamental solution has not yet been attained.

Furthermore, as other inorganic microbicides, those which comprise antimicrobial metals supported on active carbons having adsorbability have been proposed. However, in these microbicides soluble antimicrobial metal salts are merely physically adsorbed or deposited, and hence the antimicrobial metal ions rapidly dissolve away upon contact with water and the microbicides have no prolonged antimicrobial effect.

Recently, it has been proposed to use as a microbicide an antimicrobial compound comprising an antimicrobial metal ion supported on a specific zirconium phosphate such as $Ag_{0.01}H_{0.95}Li_{0.04}Zr_2(PO_4)_3$. This microbicide is chemically and physically stable and is known as a material which has long-term antifungal and antibacterial activities (Japanese Patent Kokai No. 3-83905).

However, the process for preparing the antimicrobial compound proposed in Japanese Patent Kokai No. 3-83905 uses a phosphate prepared by a dry process and according to the dry process, the antimicrobial ion can be uniformly supported on the zirconium phosphate only after a mixture of starting material powders has been fired to obtain a lumpy zirconium phosphate and then this has been crushed and ground to fine powders. Therefore, this process has the problems that it is low in productivity; additionally it is difficult to obtain a phosphate compound having uniform and fine particle size.

Moreover, this antimicrobial compound tends to color slightly when used under severe conditions such as exposure to sunlight under high temperature and high humidity. Accordingly, there is a great need to inhibit even the slight coloration for uses in which coloration must be avoided as much as possible.

The object of the present invention is to provide a process for easily producing an antimicrobial compound having uniform and fine particle size and usable as a microbicide which undergoes substantially no coloration even under severe conditions such as exposure to sunlight or high temperature or contact with acidic solutions and which can exhibit antifungal, antibacterial and antialgal activities for a long period of time, without using crushing and grinding steps which are required for preparing the phosphates by a dry process.

SUMMARY OF THE INVENTION

As a result of intensive research conducted by the inventors in an attempt to attain the above object, it has been found that in preparing an antimicrobial compound by supporting an antimicrobial metal ion on a phosphate, an antimicrobial compound which is excellent in chemical and physical stability and has long-term antifungal, antibacterial and antialgal activities can be obtained by using a phosphate compound produced by a wet process as a starting material and by firing the phosphate compound before or after supporting thereon the antimicrobial metal ion. Thus, the present invention has been accomplished.

That is, the present invention relates to a process for producing an antimicrobial compound represented by the following formula [1]:

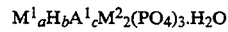  [1]

wherein $M^1$ is at least one metal ion selected from silver, copper, zinc, tin, mercury, lead, iron, cobalt, nickel, manganese, arsenic, antimony, bismuth, barium, cadmium and chromium, $A^1$ is at least one ion selected from alkali metal ion and alkaline earth metal ion, $M^2$ is a tetravalent metal, n is a number which satisfies $0 \leq n \leq 6$, a and b are positive numbers and c is 0 or a positive number, and a, b and c satisfy $ka+b+mc=1$ where k is a valence of $M^1$ and m is a valence of $A^1$, by supporting at least one metal ion selected from silver, copper, zinc, tin, mercury, lead, iron, cobalt, nickel, manganese, arsenic, antimony, bismuth, barium, cadmium and chromium on a phosphate represented by the following formula [2]:

$$A^2{}_dM^2{}_2(PO_4)_3 \cdot nH_2O \quad [2]$$

wherein $A^2$ is at least one ion selected from alkali metal ion, alkaline earth metal ion and ammonium ion, $M^2$ and n are as defined above and d is $1/m'$ where $m'$ is a valence of $A^2$, characterized in that said phosphate is synthesized by a wet process and furthermore characterized in that a step of supporting hydrogen ion and a step of firing at 500° to 1300° C. are employed.

DETAILED DESCRIPTION OF THE INVENTION

The starting material, firing method and other procedures used in the present invention are explained in detail below.

Phosphates

The phosphate compounds used as a starting material in the present invention are those which are represented by the above formula [2], and are amorphous compounds or crystalline compounds belonging to the space group R3c in which the constituting ions form a three-dimensional network structure.

As the phosphates used in the present invention, preferred are the crystalline compounds having the three-dimensional network structure in view of less discoloration upon exposure to sunlight.

$A^2$ in the above formula is an alkali metal ion, an alkaline earth metal ion, or ammonium ion, and preferred examples of the alkali metal ion and the alkaline earth metal ion are lithium, sodium, potassium, magnesium and calcium.

Preferred ions as $A^2$ are lithium ion, sodium ion and ammonium ion in consideration of stability of the resulting compounds and their cheapness, and sodium ion is especially preferred.

$M^2$ in the formula [2] is a tetravalent metal and is preferably zirconium, titanium or tin, and zirconium and titanium are especially preferred in consideration of stability of the resulting compounds.

Examples of the phosphate represented by the above formula [2] [hereinafter referred to as "phosphate (2)"] are as follows:

$Li_1Zr_2(PO_4)_3$
$(NH_4)_1Zr_2(PO_4)_3$
$Na_1Zr_2(PO_4)_3$
$K_1Ti_2(PO_4)_3$

The phosphate (2) used in the present invention is a compound synthesized by a wet process. By employing the wet synthesis process, the phosphate (2) having uniform and fine particle size can be easily obtained only by light disintegration without grinding step, and an antimicrobial compound having uniform and fine particle size can be obtained by supporting an antimicrobial metal ion on the resulting phosphate (2).

All of the known wet synthesis processes can be employed. Specifically, for example, there is a wet process conducted under atmospheric pressure or under application of pressure.

The tetravalent metal phosphate compounds are obtained by reacting phosphate ion with a tetravalent metal ion in water in the presence of at least one ion selected from an alkali metal ion, an alkaline earth metal ion and ammonium ion.

Compounds having alkali metal ion, alkaline earth metal ion or ammonium ion are unlimited as far as they have said ion, but preferred are hydroxides, sulfates, nitrates, chlorides, carbonates, hydrogen-carbonates, phosphates and borates.

The reaction of phosphate ion with a tetravalent metal ion can be performed by merely reacting compounds having these ions. However, for promoting this reaction, it is preferred to previously form a mixture of a compound having a tetravalent metal ion (hereinafter referred to as "tetravalent metal compound") and a carboxylic acid or a salt thereof and to react this mixture with a compound having phosphate ion.

The mixing ratio of the carboxylic acid or salt thereof and the tetravalent metal compound is preferably 1 equivalent of the carboxylic acid or salt thereof (molecular weight per carboxyl group) per equivalent of the trivalent metal compound (formula weight per tetravalent metal atom).

The tetravalent metal compounds usable for the above-mentioned process are suitably those which are water-soluble or acid-soluble. Examples of the preferred tetravalent metal compounds containing zirconium as a tetravalent metal are zirconium nitrate, zirconium acetate, zirconium sulfate, basic zirconium sulfate, zirconium oxysulfate and zirconium oxychloride.

The carboxylic acid or salt thereof is preferably an aliphatic polycarboxylic acid having at least two carboxyl groups or salt thereof. Examples thereof are shown below.

That is, they include aliphatic dibasic acids such as oxalic acid, maleic acid, malonic acid and succinic acid, salts of aliphatic dibasic acids such as sodium oxalate, sodium hydrogen oxalate, lithium hydrogen oxalate, ammonium oxalate and ammonium hydrogen oxalate, and aliphatic hydroxycarboxylic acids such as citric acid, tartaric acid and malic acid and salts thereof.

Among them, oxalic acid and sodium and ammonium salts thereof are especially preferred.

The phosphoric acid or salt thereof used as a compound having phosphate ion is preferably in the form of an aqueous solution previously prepared.

As the preferred phosphates there are ammonium phosphate and alkali metal phosphates which are water-soluble or acid-soluble salts. Examples thereof are sodium dihydrogenphosphate, disodium hydrogenphosphate, trisodium phosphate, diammonium hydrogenphosphate, ammonium dihydrogenphosphate and dipotassium hydrogenphosphate.

In carrying out the reaction, the ratio of the tetravalent metal ion and the phosphate ion is preferably 0.4–4.0 equivalents, more preferably 0.6–2.0 equivalents and most preferably 0.6–0.8 equivalent of the tetravalent metal ion per equivalent of the phosphate ion.

When the equivalent ratio is less than 0.4 or more than 4.0, there is a possibility of producing a compound having the structure which is not preferred to be used in the present invention.

A particulate tetravalent metal phosphate is precipitated by the above-mentioned reaction to give a slurry of the reaction product. Then, preferably the pH of the slurry is adjusted to 7 or less by addition of an acid or an alkali. In order to obtain a tetravalent metal phosphate of high crystallinity, it is desired that the pH of the slurry is adjusted to preferably 1–6, more preferably 2–6 and the slurry is heated to preferably 80° C. or higher, more preferably 95° C. or higher. When the slurry is heated to lower than 80° C., there is a possibility of producing a compound having the structure which is not preferred, but when it is heated to higher than 95° C., crystallization proceeds in a short time. Since the crystallization rate increases with increase in the temperature, the heating temperature is more preferably 97°–100° C. under atmospheric pressure and further preferably 110°–200° C. under pressure, namely, under saturated water vapor pressure. Within this range of the temperature, the crystallization is completed usually in 2–50 hours.

In consideration of agitatability of the slurry of the reaction product, the solid concentration of the slurry is preferably 15% by weight or less.

The reaction product is separated from the liquid phase by the known separation means such as filtration, decantation, centrifugal separation, filter press and cross flow filtration system, washed and dried by conventional methods and, if necessary, disintegrated to obtain a tetravalent metal phosphate.

An actual example of synthesis of the phosphate (2) used in the present invention is as follows: 9 g of oxalic acid is dissolved in an aqueous solution prepared by dissolving 46.1 g of zirconium oxychloride in 252 g of pure water under stirring. To the resulting solution is added 24.7 g of 85% phosphoric acid to produce a precipitate. The reaction mixture is adjusted to pH 3 with 15% aqueous sodium hydroxide solution and heated and refluxed at 97° C. for 10 hours. Then, the precipitate is subjected to filtration and washing with water until the electric conductivity EC reaches 100 $\mu$S/cm or less, and dried at 110° C. This is further disintegrated to primary particles by a disintegrator.

Supporting of Antimicrobial Metal Ions

At least one antimicrobial metal ion selected from silver, copper, zinc, tin, mercury, lead, iron, cobalt, nickel, manganese, arsenic, antimony, bismuth, barium, cadmium and chromium is supported on the phosphate (2) obtained as mentioned above, before or after firing.

These antimicrobial metal ions $M^1$ are all known as metal ions having antifungal, antibacterial and antialgal activities. Among them, silver ion is especially effective from the point of safety and besides, as a metal ion capable of enhancing antifungal, antibacterial and antialgal activities.

For supporting the antimicrobial metal ion on the phosphate (2), there is used, for example, ion-exchange reaction which utilizes ion-exchange characteristics of the phosphate.

The ion-exchange reaction can be carried out according to conventionally well known methods, and can be allowed to easily proceed by immersing a phosphate compound in an aqueous nitric acid solution containing a suitable concentration of the antimicrobial metal ion. The amount a of the antimicrobial metal ion to be supported can be readily adjusted depending on the necessary properties and the conditions for use by increasing the concentration of the antimicrobial metal ion in the aqueous solution in which the phosphate compound before or after firing is immersed. Furthermore, the amount to be supported can be somewhat increased by carrying out adjustments such as prolongation of the period for which the phosphate compound is immersed in the antimicrobial metal ion-exchanging solution or increase of the immersing temperature.

More specific conditions for the ion exchange reaction are as follows. The tetravalent metal phosphate is immersed in an aqueous solution of an antimicrobial metal ion set at 0°–100° C. preferably 40°–100° C. for several minutes to several ten minutes, preferably for a longer time (for example, 1 to several hours) so that the solution reaches such a solid concentration as the solution can be smoothly agitated, for example, 40% by weight or less, preferably 5–20% by weight. Further specifically, for example, the antimicrobial phosphate can be prepared in the following manner; 10% by weight of a phosphate compound is added to 1% by weight of aqueous silver nitrate solution and the mixture is stirred at 40° C. for 4 hours and then filtrated. The residue is washed with water until the electric conductivity EC reaches 100 $\mu$S/cm or less and dried at 110° C. for 12 hours.

For exhibiting the antifungal, antibacterial and antialgal activities, the larger value a is preferred, but when the value a is 0.001 or more, the antifungal, antibacterial and antialgal activities can be sufficiently exhibited. However, in consideration of the fact that when the value a is smaller than 0.01, it may become difficult to exhibit the antifungal, antibacterial and antialgal activities for a prolonged period of time, and furthermore from the economical viewpoint, the value a is preferably in the range of 0.01 to 0.5, more preferably 0.10 to 0.30.

The antimicrobial compound obtained by supporting the antimicrobial metal ion on the phosphate (2) is represented by the formula [1], and is an amorphous compound or a crystalline compound belonging to the space group R3c in which the constituting ions form a three-dimensional network structure.

As the antimicrobial phosphate compounds obtained in the present invention, preferred are the crystalline compounds having the three-dimensional network structure in view of less discoloration when exposed to sunlight.

Examples of the antimicrobial phosphate obtained by supporting the antimicrobial metal are enumerated below.

$Ag_{0.005}H_{0.995}Zr_2(PO_4)_3$
$Ag_{0.01}(NH_4)_{0.99}Zr_2(PO_4)_3$
$Ag_{0.05}Na_{0.95}Zr_2(PO_4)_3$
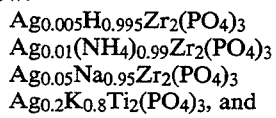
$Ag_{0.2}K_{0.8}Ti_2(PO_4)_3$, and
compounds having the above formulas in which Ag is replaced with Zn, Mn, Ni, Pb, Hg, Sn or Cu so that they have the same electric charge amount as that of the silver ion per mol of the compounds.

Firing Method

It is necessary in the present invention to fire the phosphate (2) or the antimicrobial compound obtained by supporting the antimicrobial metal ion at 500°–1300° C., preferably 600°–1000° C., more preferably 700°–900° C. Through this firing step, chemical and physical stability of microbicides consisting of said antimicrobial compounds can be markedly improved and thus, microbicides having extremely excellent weathering resistance can be obtained.

If the firing is carried out at a temperature lower than 500° C. or higher than 1300° C., the antimicrobial activity decreases or it becomes difficult to sufficiently exhibit the effect to improve the chemical and physical stability. Accordingly, it is utterly impossible to exhibit the effect of the present invention, when a mere drying step which is generally conducted at 70°–130° C. is carried out after synthesis of the phosphate by a wet process.

The firing time is not critical and the effect of the present invention can be sufficiently exhibited by carrying out the firing usually for 1-20 hours.

Heating rate and cooling rate are not critical either and can be readily adjusted in consideration of the capability and productivity of a firing furnace.

Supporting of Hydrogen Ion

In order to obtain microbicides extremely excellent in antimicrobial activity and weather resistance, it is necessary to support hydrogen ion together with the antimicrobial metal ion.

When the starting tetravalent metal phosphate contains ammonium ion, the ammonium ion is thermally decomposed by carrying out the firing step to leave hydrogen ion, and therefore the microbicides on which hydrogen ion is supported can be obtained merely by carrying out the firing step. Preferable firing conditions in this case are a firing temperature in the range of 600°-1100° C. and a firing time in the range of about 0.5-2 hours.

On the other hand, when the tetravalent metal phosphate does not contain ammonium ion, a step for supporting hydrogen ion must be added and the typical methods include a method of immersing the tetravalent metal phosphate or a microbicide containing no hydrogen ion in an acid solution. This method is higher in productivity than the above-mentioned method of firing the tetravalent metal phosphate containing ammonium ion.

Preferred examples of the acid solution in which the tetravalent metal phosphate or a microbicide containing no hydrogen ion is immersed, are hydrochloric acid and sulfuric acid, and especially preferred is nitric acid. Acid concentration of the acid solution, immersing temperature and immersing time are unlimited, but generally hydrogen ion can be supported in a short time at a higher acid concentration and at a higher temperature. Therefore, the acid concentration is preferably 0.1N or higher and more preferably 0.3N or higher, the treating temperature is preferably 40° C. or higher and more preferably 60°-100° C., and the immersing time is preferably 10 minutes or more and more preferably 60 minutes or more.

The amount (b) of hydrogen ion to be supported is preferably 0.3 or more, more preferably 0.40-0.70, most preferably 0.50-0.60.

The order of the step of supporting hydrogen ion, the step of supporting the antimicrobial ion and the step of firing has no special limitation, but it is preferred to carry out the steps in the above-mentioned order or to simultaneously carry out the supporting of hydrogen ion and that of antimicrobial ion and then carry out the firing.

Examples of the antimicrobial compounds of the formula [1] are as follows.

$Ag_{0.16}H_{0.84}Zr_2(PO_4)_3$ 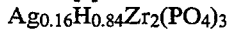

$Ag_{0.05}H_{0.05}Na_{0.90}Zr_2(PO_4)_3$ 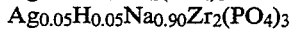

$Ag_{0.05}H_{0.55}NaO_{0.40}Zr_2(PO_4)_3$, and 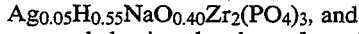

compounds having the above formulas in which Ag is replaced with Zn, Mn, Ni, Pb, Hg, Sn or Cu so that they have the same electric charge amount as that of the silver ion per mol of the compounds.

The microbicides obtained in this way are stable against exposure to heat and light and undergo no change in structure and composition even after heated to 500° C. and 800°-1100° C. in some cases, and further-more show no discoloration by irradiation with ultraviolet rays.

Furthermore, no change is seen in the skeleton structure even in an acidic solution. Therefore, the antimicrobial phosphates of the present invention are not restricted by conditions such as heating temperature and light-proof conditions when they are processed for obtaining various molded products and are stored and used, while the conventional microbicides have been restricted by them.

The form of the antimicrobial compounds of the present invention in use is unlimited, and they can be optionally mixed with other components or formed into composites with other materials depending on uses.

For example, the antimicrobial compounds of the present invention can be used in various forms such as powders, powder-containing dispersions, powder-containing particles, powder-containing paints, powder-containing fibers, powder-containing papers, powder-containing plastics, powder-containing films and powder-containing aerosols. Furthermore, if necessary, they can be used in combination with various additives or materials for deodorizers, flame-proof agents, corrosion-proof agents, fertilizers and building materials.

The microbicides containing the antimicrobial compound obtained by the present invention as an active ingredient can exhibit antifungal, antibacterial and antialgal activities for any use against fungi, bacteria and algae on which the antimicrobial metal ions such as silver ion effectively act, and can be effectively used, for example, for the following uses: fibers such as working clothes, medical clothes, medical beddings, medical appliances, sports wear, medical dressings, fishing nets, curtains, carpets, underwears, and air filters; papers such as wall papers; daily sundries made of resin shaped articles of kitchen utensils such as strainers and resin chopping boards; films such as food-packaging films, medical films, and synthetic leathers; paints such as paints for sterilizers, corrosion-resistant paints, and antifungal paints; powders such as agricultural soil; and liquid compositions such as shampoo.

According to the present invention, the phosphate compounds are prepared by a wet process, and therefore microbicides having a uniform and fine particle size can be easily obtained, and the grinding step which is needed for synthesis of phosphate compounds by a dry process is not needed, and lightly disintegrating the fired product after the firing step is sufficient in the present invention.

Since the antimicrobial compounds obtained by the process of the present invention are chemically and physically very stable, various shaped products comprising mixtures of various resins with these compounds as microbicides show substantially no coloration even under severe conditions such as exposure to sunlight or an atmosphere of high temperatures or contact with acidic solutions, and have long-term antifungal, antibacterial and antialgal activities. Thus, they have excellent effects and are very useful.

In the following examples and comparative examples, analysis of the composition, weathering test and antimicrobial activity test of the microbicides were conducted under the following conditions.

Analysis of Composition

The zirconium phosphate salt containing silver ion was dissolved in a small amount of hydrofluoric acid to prepare a test solution. Then, silver and sodium concentrations in the test solution were measured by atomic absorption spectrometry.

Furthermore, concentration of ammonium ion in the test solution was measured by indophenol absorption spectrophotometry.

Weathering Test

In Examples 1-3 and Comparative Example 1, a plate of 5 mm thickness consisting of a commercially available polyethylene resin [HIZEX 2100JP (tradename for high-density polyethylene powders manufactured by Mitsui Petrochemical Industries, Ltd.)] which contained 10 parts by weight of the microbicide per 100 parts by weight of the resin, was prepared and subjected to 3 cycles of weathering test (1 cycle comprising the steps of irradiating the sample with ultraviolet ray for 1 hour at 60° C. and then leaving it for 1 hour at 40° C. and a humidity of 95%). Then, the weathering resistance was evaluated by measuring the color of the sample before and after the test by a calorimeter.

In Examples 4-6 and Comparative Examples 2-4, in order that discoloration of the plate in the weathering test can be evaluated at high sensitivity, the content of the microbicide in the plate and the thickness of the plate were changed. That is, a plate of 3 mm thickness of the same commercially available polyethylene resin as above which contained 5 parts by weight of the microbicide per 100 parts by weight of the resin, was prepared. The resulting antimicrobial plates were subjected to 3 cycles of weathering test using a weathering tester UC-1 manufactured by Toyo Seiki Mfg. Co. (one cycle of the test using UC-1 was conducted for 2 hours and comprised the step of irradiating the sample with ultraviolet radiation of not more than 350 nm at 60° C. for 1 hour and the step of leaving the sample in an atmosphere of 95% or higher in humidity at 40° C. for 1 hour). The color of the sample before and after the test was measured by color-difference meter SZ-Σ80 manufactured by Nihon Denshoku Kogyo Co., Ltd., and color difference ($\Delta E$) was obtained from the following formula.

$$\Delta E = \{(L_0 - L_1)^2 + (a_0 - a_1)^2 + (b_0 - b_1)^2\}^{\frac{1}{2}}$$

$L_0$, $a_0$, $b_0$: Color before the test
$L_1$, $a_1$, $b_1$: Color after the test Antimicrobial Activity Test Antimicrobial activity test of silver zirconium phosphate against *Escherichia coli* was conducted in accordance with the standard method of Japan Chemical Remedy Society to measure the minimum inhibitory concentration (MIC).

REFERENTIAL EXAMPLE 1

80 g of 6% aqueous oxalic acid solution was added to an aqueous solution prepared by dissolving 116.5 g of zirconium oxychloride ($ZrOCl_2 \cdot 8H_2O$) and 2.9 g of ammonium chloride in 183 g of pure water under stirring, and 19 g of 85% phosphoric acid was further added. The reaction mixture was adjusted to pH 3.5 with an aqueous ammonia solution and heated and refluxed at 97° C. for 78 hours. Then, the precipitate was subjected to filtration and washing with water until the electric conductivity EC of the filtrate reached 100 μS/cm or less. The residue was dried at 110° C. for 12 hours and then disintegrated to a given particle size by a disintegrator to obtain zirconium phosphate [$(NH_4)Zr_2(PO_4)_3$] having a network structure.

EXAMPLE 1

10 g of the phosphate compound obtained in the Referential Example 1 was fired at 800°, 900° or 1000° C. for 4 hours in a firing furnace (heating rate: 200° C./Hr). The fired product was stirred in 100 cc of 1% aqueous silver nitrate solution for 4 hours and then washed with water until the electric conductivity reached 100 μS/cm or less and dried at 105° C. for 12 hours to obtain the three antimicrobial compounds having the following compositional formula (a).

$$Ag_{0.16}H_{0.84}Zr_2(PO_4)_3 \tag{a}$$

These antimicrobial compounds were subjected to the weathering test as microbicides. As clear from Table 1 which shows the value L before and after the test, all of them were excellent in weathering resistance as microbicides.

Furthermore, as a result of the antimicrobial activity test, it was found that the minimum inhibitory concentration (MIC) for *Escherichia coli* was 125 ppm for all of the microbicides.

TABLE 1

| Firing temperature | Firing time | $L_0$ | $L_1$ |
|---|---|---|---|
| 800° C. | 4 hr | 76 | 67 |
| 900° C. | 4 hr | 80 | 77 |
| 1000° C. | 4 hr | 81 | 77 |

EXAMPLE 2

The compound having the above composition formula (a) prepared in accordance with the Referential Example 1 and Example 1 except that the firing was not carried out, was fired at 800°, 900° or 1000° C. for 4 or 10 hours in a firing furnace and disintegrated by a disintegrator to obtain three antimicrobial compounds.

These antimicrobial compounds were subjected to the weathering test. As apparent from Table 2 which shows the value L before and after the test, all of the microbicides were excellent in weathering resistance.

As a result of the antimicrobial activity test, it was found that the minimum inhibitory concentration (MIC) for *Escherichia coli* was 125 ppm for all of the microbicides.

TABLE 2

| Firing temperature | Firing time | $L_0$ | $L_1$ |
|---|---|---|---|
| 800° C. | 4 hr | 86 | 67 |
| 900° C. | 4 hr | 86 | 80 |
| 1000° C. | 10 hr | 87 | 81 |

Example 3

The following phosphate obtained in the same manner as in Example 2 was fired at 800°, 900° or 1000° C. for 4 hours in a firing furnace and then disintegrated by a disintegrator to obtain three antimicrobial compounds.

$$Ag_{0.16}(NH_4)_{0.84}Zr_2(PO_4)_3$$

These antimicrobial compounds were subjected to the weathering test. As apparent from Table 3 which shows the value L before and after the test, all of the microbicides were excellent in weathering resistance.

As a result of the antimicrobial activity test, it was found that the minimum inhibitory concentration (MIC) for *Escherichia coli* was 125 ppm for all of the microbicides.

TABLE 3

| Firing temperature | Firing time | $L_0$ | $L_1$ |
|---|---|---|---|
| 800° C. | 4 hr | 78 | 73 |
| 900° C. | 4 hr | 73 | 70 |
| 1000° C. | 4 hr | 83 | 80 |

COMPARATIVE EXAMPLE 1

The following phosphate compound was subjected to the weathering test without subjecting it to the firing. The value $L_o$ before the weathering test was 68 and the value $L_1$ after the test was 28, and coloration was seen.

$Ag_{0.16}(NH_4)_{0.84}Zr_2(PO_4)_3$

As a result of the antimicrobial activity test, the minimum inhibitory concentration (MIC) for *Escherichia coli* was 125 ppm.

REFERENTIAL EXAMPLE 2

Preparation of K Type Zirconium Phosphate Salt

Oxalic acid (0.1 mol) was added to an aqueous solution of zirconium oxychloride (0.2 mol) with stirring, and thereto was further added phosphoric acid (0.3 mol) (equivalent of zirconium ion per equivalent of phosphate ion was 0.67). The reaction mixture was adjusted to pH 3.5 with aqueous potassium hydroxide solution and heated and refluxed at 95° C. for 20 hours and then, the precipitate was subjected to filtration, washing with water and drying to obtain potassium zirconium phosphate [$KZr_2(PO_4)_3 \cdot 1.2H_2O$] having a network structure (average particle size: 0.4 μm).

REFERENTIAL EXAMPLE 3

Preparation of $NH_4$ Type Zirconium Phosphate Salt

Ammonium chloride (0.1 mol) and oxalic acid (0.1 mol) were added to an aqueous solution of zirconium oxychloride (0.2 mol) with stirring, and thereto was further added phosphoric acid (0.3 mol). The reaction mixture was adjusted to pH 4.0 with aqueous ammonia solution and heated and refluxed at 95° C. for 48 hours and then, the precipitate was subjected to filtration, washing with water and drying to obtain ammonium zirconium phosphate [$NH_4Zr_2(PO_4)_3 \cdot 1.1H_2O$] having a network structure (average particle size: 0.7 μm).

REFERENTIAL EXAMPLE 4

Preparation of Na Type Zirconium Phosphate Salt

Oxalic acid (0.1 mol) was added to an aqueous solution of zirconium oxychloride (0.2 mol) with stirring and thereto was further added phosphoric acid (0.3 mol). The reaction mixture was adjusted to pH 3.5 with aqueous sodium hydroxide solution and heated and refluxed at 95° C. for 10 hours and then, the precipitate was subjected to filtration, washing with water and drying to obtain sodium zirconium phosphate [$NaZr_2(PO_4)_3 \cdot 1.1H_2O$] having a network structure (average particle size: 0.8 μm).

EXAMPLE 4

Each of the K type zirconium phosphate powder prepared in Referential Example 2 and the Na type zirconium phosphate powder prepared in Referential Example 4 was added to a 1N nitric acid solution containing silver ion and stirred at 60° C. for 10 hours. Thereafter, the resulting slurry was filtered and the residue was sufficiently washed with pure water, further heated and dried at 110° C. overnight and then fired at 750° C. for 4 hours to obtain a microbicide (Sample Nos. 1 and 3).

EXAMPLE 5

The $NH_4$ type zirconium phosphate powder prepared in Referential Example 3 was fired at 700° C. for 4 hours to obtain a hydrogen type zirconium phosphate [$HZr_2(PO_4)_3$]. This was added to a 1N nitric acid solution containing silver ion and stirred at 60° C. for 10 hours. Thereafter, the resulting slurry was filtered, and the residue was sufficiently washed with pure water, further heated and dried at 110° C. overnight and then fired at 750° C. for 4 hours to obtain a microbicide (Sample No. 2).

EXAMPLE 6

The Na type zirconium phosphate powder prepared in Referential Example 4 was added to a 0.1N nitric acid solution containing silver ion and stirred at 60° C. for 10 hours. Thereafter, the resulting slurry was filtered and the residue was sufficiently washed with pure water, further heated and dried at 110° C. overnight and then fired at 750° C. for 4 hours to obtain a microbicide (Sample No. 4).

COMPARATIVE EXAMPLE 2

The Na type zirconium phosphate powder prepared in Referential Example 4 was added to a 1N nitric acid solution containing a given amount of silver nitrate and stirred at 60° C. for 10 hours. Thereafter, the resulting slurry was filtered and the residue was sufficiently washed with pure water. This was only heated and dried at 110° C. overnight and subjected to no firing to obtain a microbicide (Sample No. 5).

COMPARATIVE EXAMPLE 3

Hydroxyapatite [$Ca_{10}(PO_4)_6(OH)_2$] or an A type zeolite (composition: $0.94Na_2O \cdot Al_2O_3 \cdot 1.92SiO_2 \cdot xH_2O$*) was added to an aqueous solution of silver nitrate alone or of silver nitrate and ammonium nitrate, stirred at room temperature for 10 hours, then sufficiently washed with water and dried at 110° C. to obtain antimicrobial hydroxyapatite (average particle size: 1.2 μm) and antimicrobial zeolite (average particle size: 2.6 μm) (Sample Nos. 6 to 8). (*: x=1 to 4)

COMPARATIVE EXAMPLE 4

The antimicrobial hydroxyapatite powder (Sample No. 6) and antimicrobial zeolite powder (Sample No. 7) obtained in Comparative Example 3 were fired at 750° C. for 4 hours (Sample Nos. 9 and 10).

The microbicides prepared as mentioned above are shown in the following Table 4.

TABLE 4

| Sample No. | Microbicides |
|---|---|
| 1 | $Ag_{0.05}K_{0.75}H_{0.20}Zr_2(PO_4)_3$ |
| 2 | $Ag_{0.10}H_{0.90}Zr_2(PO_4)_3$ |
| 3 | $Ag_{0.19}Na_{0.47}H_{0.34}Zr_2(PO_4)_3$ |
| 4 | $Ag_{0.20}Na_{0.7}H_{0.10}Zr_2(PO_4)_3$ |
| 5 | $Ag_{0.19}Na_{0.47}H_{0.34}Zr_2(PO_4)_3 \cdot 1.2H_2O$ |

TABLE 4-continued

| Sample No. | Microbicides |
|---|---|
| 6 | $Ag_{0.16}Ca_{9.92}(PO_4)_6(OH)_2$ |
| 7 | $0.04Ag_2O \cdot 0.9Na_2O \cdot Al_2O_3 \cdot 1.9SiO_2 \cdot 2.2H_2O$ |
| 8 | $0.04Ag_2O \cdot 0.02(NH_4)_2O \cdot 0.8Na_2O \cdot Al_2O_3 \cdot 1.9SiO_2 \cdot 2.7H_2O$ |
| 9 | (Fired product of Sample No. 6) |
| 10 | (Fired product of Sample No. 7) |

Preparation of Antimicrobial Plates and Evaluation Thereof

Antimicrobial plates were prepared using the various microbicides prepared in Examples 4 to 6 and Comparative Examples 2 to 4 in the manner as mentioned in the above item of weathering test.

The results of the antimicrobial activity test and the weathering test on these antimicrobial plates are shown in the following Table 5.

TABLE 5

| Sample No. | Color (before test) | | | Color (after test) | | | Color difference $\Delta E$ | MIC (ppm) |
|---|---|---|---|---|---|---|---|---|
| | $L_0$ | $a_0$ | $b_0$ | $L_1$ | $a_1$ | $b_1$ | | |
| 1 | 52.68 | −1.83 | −4.20 | 51.89 | −1.46 | −3.46 | 1.9 | 250 |
| 2 | 55.23 | −1.21 | −5.12 | 55.07 | −1.40 | −3.00 | 2.1 | 250 |
| 3 | 54.64 | −1.07 | −4.71 | 54.39 | −1.06 | −2.42 | 2.3 | 62.5 |
| 4 | 55.69 | −0.69 | −5.71 | 53.90 | −0.88 | 1.76 | 7.7 | 62.5 |
| 5 | 62.54 | −1.51 | −3.59 | 37.92 | 7.38 | 16.63 | 33.1 | 250 |
| 6 | 37.49 | −0.60 | 7.25 | 24.57 | 0.92 | 3.80 | 13.5 | 250 |
| 7 | 53.59 | −1.90 | −1.52 | 30.43 | 7.50 | 9.51 | 27.3 | 250 |
| 8 | 53.27 | −1.50 | −1.78 | 30.29 | 6.89 | 10.52 | 27.4 | 250 |
| 9 | 48.48 | −0.74 | −1.29 | 47.42 | −0.53 | 0.05 | 1.7 | >2000 |
| 10 | 35.73 | −1.05 | −0.38 | 37.37 | −0.75 | 2.88 | 3.7 | >2000 |

As clear from the results of the above Table 5, the microbicides of the present invention (Sample Nos. 1, 2, 3 and 4) are excellent in both the antimicrobial activity and the weathering resistance.

On the other hand, the microbicide (Sample No. 5) which was not subjected to the firing even though prepared by supporting silver ion on the zirconium phosphate salt, has problem in the weathering resistance.

In the case of the antimicrobial hydroxyapatite, the unfired product (Sample No. 6) colored just after molded into an antimicrobial plate, and furthermore had problem in the weathering resistance, and the fired product (Sample No. 9) was very low in the antimicrobial activity.

In the case of the antimicrobial zeolite, the unfired product (Sample Nos. 7 and 8) had problem in the weathering resistance, and the fired product (Sample No. 10) colored just after molded into an antimicrobial plate and furthermore was very low in the antimicrobial activity.

EXAMPLE 7

Zirconium sulfate (0.12 mol), ammonium sulfate (0.04 mol), phosphoric acid (0.18 mol) and sodium hydroxide (0.018 mol) under mixing were added to pure water (40 g) to prepare a homogeneous aqueous solution. This reaction mixture was heated for 4 hours under saturated water vapor pressure at 120° C., and the precipitate was subjected to filtration, washing with water and drying to obtain a zirconium phosphate salt having a network structure. This was added to an aqueous silver nitrate solution containing a given amount of silver ion and stirred at 60° C. for 10 hours. Then, the slurry was filtrated, and the residue was sufficiently washed with pure water, heated and dried at 110° C. overnight and fired at 900° C. for 4 hours to obtain a microbicide having the following composition (Sample No. 11).

$$Ag_{0.15}Na_{0.05}(NH_4)_{0.80}Zr_2(PO_4)_3$$

The microbicide of Sample No. 11 obtained above was evaluated on the weathering resistance and the antimicrobial activity in the same manner as the evaluation of the microbicide obtained in Example 4, and the results are shown in Table 6.

COMPARATIVE EXAMPLE 5

A microbicide (Sample No. 12) was prepared in the same manner as in Example 7 except that the firing at 900° C. was not carried out.

The microbicide of Sample No. 12 obtained above was evaluated on the weathering resistance and the antimicrobial activity in the same manner as the evaluation of the microbicide obtained in Example 4 and the results are shown in Table 6.

TABLE 6

| Sample No. | Color (before test) | | | Color (after test) | | | Color difference $\Delta E$ | MIC (ppm) |
|---|---|---|---|---|---|---|---|---|
| | $L_0$ | $a_0$ | $b_0$ | $L_1$ | $a_1$ | $b_1$ | | |
| 11 | 70.92 | 1.24 | 5.74 | 66.18 | 2.15 | 11.01 | 7.2 | 250 |
| 12 | 71.69 | 0.37 | 5.18 | 40.49 | 8.27 | 10.96 | 32.9 | 250 |

As apparent from the above Table 6, also when the zirconium phosphate was synthesized by a hydrothermal process, the weathering resistance of the microbicide could be improved by carrying out the firing.

What is claimed is:

1. In a process for producing an antimicrobial compound represented by the following formula [1]:

$$M^1_a H_b A^1_c M^2(PO_4)_3 \cdot nH_2O \qquad [1]$$

wherein $M^1$ is at least one metal ion selected from the group consisting of silver, copper, zinc, tin, mercury, lead, iron, cobalt, nickel, manganese, arsenic, antimony, bismuth, barium, cadmium and chromium, $A^1$ is at least one ion selected from the group consisting of alkali metal ion and alkaline earth metal ion, $M^2$ is a tetravalent metal, n is a number which satisfies $0 \leq n \leq 6$, a and b are positive numbers and c is 0 or a positive number, and a, b and c satisfy $ka+b+mc=1$ where k is a valence of $M^1$ and m is a valence of $A^1$, by adding at least one metal ion selected from the group consisting of silver, copper, zinc, tin, mercury, lead, iron, cobalt, nickel, manganese, arsenic, antimony, bismuth, barium, cadmium and chromium to a phosphate represented by the following formula [2]:

$$A^2{}_dM^2{}_2(PO_4)_3 \cdot nH_2O \qquad [2]$$

wherein $A^2$ is at least one ion selected from the group consisting of alkali metal ion, alkaline earth metal ion and ammonium ion, $M^2$ and n are as defined above and d is $1/m'$ where $m'$ is a valence of $A^2$, the improvement comprising synthesizing said phosphate of formula 2 by a wet process, adding hydrogen ion to said phosphate, adding said at least one metal ion $M^1$ to said phosphate to produce an antimicrobial phosphate and, firing the antimicrobial phosphate at 500° to 1300° C.

2. A process according to claim 1, wherein the phosphate is a crystalline compound having a three-dimensional network structure and represented by the formula [2] in which $A^2$ is sodium ion and $M^2$ is zirconium or titanium.

3. A process according to claim 1, wherein the antimicrobial compound is a crystalline compound having a three-dimensional network structure and represented by the formula [1] in which $M^1$ is silver ion, a is 0.01 to 0.5, $A^1$ is sodium ion, and $M^2$ is zirconium or titanium.

4. A process according to claim 1 wherein when the phosphate represented by formula 2 contains ammonium ion, the step of adding hydrogen ion is carried out by thermally decomposing the ammonium ion in the phosphate represented by formula 2 in the firing step to leave hydrogen ion in the compound formed in the firing step.

5. A process according to claim 1 wherein when the phosphate represented by formula 2 does not contain ammonium ion, the step of adding hydrogen ion is carried out by immersing the phosphate represented by formula 2 in an acid solution.

6. In a process for producing an antimicrobial compound represented by the following formula:

$$M^1{}_aH_bA^1{}_cM^2{}_2(PO_4)_3 \cdot nH_2O \qquad [1]$$

wherein $M^1$ is at least one metal ion selected from the group consisting of silver, copper, zinc, tin, mercury, lead, iron, cobalt, nickel, manganese, arsenic, antimony, bismuth, barium, cadmium and chromium, $A^1$ is at least one ion selected from the group consisting of alkali metal ion and alkaline earth metal ion, $M^2$ is a tetravalent metal, n is a number which satisfies $0 \leq n \leq 6$, a and b are positive numbers and c is 0 or a positive number, and a, b, and c satisfy $ka+b+mc=1$ wherein k is the valence of $M^1$ and m is the valence of $A^1$, by adding at least one metal ion selected from the group consisting of sliver, copper, zinc, tin, mercury, lead, iron, cobalt, nickel, manganese, arsenic, antimony, bismuth, barium, cadmium and chromium to a phosphate represented by the following formula:

$$A^2{}_dM^2{}_2(PO_4)_3 \cdot nH_2O \qquad [2]$$

wherein $A^2$ is at least one ion selected from the group consisting of alkali metal ion, alkaline earth metal ion and ammonium ion, $M^2$ and n are as defined above and d is $1/m'$, where $m'$ is the valence of $A^2$, the improvement comprising synthesizing the phosphate of formula [2] by a wet process, adding said at least one metal ion M1 and hydrogen ion simultaneously to said phosphate to produce an antimicrobial phosphate, then firing said antimicrobial phosphate at a temperature of from 500° to 1300° C.

7. A process according to claim 6 wherein the phosphate is a crystalline compound having a three-dimensional network structure and represented by the formula [2] in which $A^2$ is sodium ion and $M^2$ is zirconium or titanium.

8. A process according to claim 6 wherein the antimicrobial compound is a crystalline compound having a three-dimensional network structure and represented by the formula [1] in which $M^1$ is silver ion, a is 0.01 to 0.5, $A^1$ is sodium ion, and $M^2$ is zirconium or titanium.

9. A process according to claim 6 wherein the phosphate represented by formula 2 contains ammonium ion, the step of adding hydrogen ion is carried out by thermally decomposing the ammonium ion in the phosphate represented by formula 2 in the firing step to leave hydrogen ion in the compound formed in the firing step.

10. A process according to claim 6 wherein when the phosphate represented by formula 2 does not contain ammonium ion, the step of adding hydrogen ion is carried out by immersing the phosphate represented by formula 2 in an acid solution.

* * * * *